(12) United States Patent
Park

(10) Patent No.: US 11,965,155 B2
(45) Date of Patent: Apr. 23, 2024

(54) BIOLOGICAL MATERIAL EXTRACTION APPARATUS

(71) Applicant: Eun Yong Park, Seongnam-si (KR)

(72) Inventor: Eun Yong Park, Seongnam-si (KR)

( * ) Notice: Subject to any disclaimer, the term of this patent is extended or adjusted under 35 U.S.C. 154(b) by 896 days.

(21) Appl. No.: 16/962,205

(22) PCT Filed: Jan. 23, 2019

(86) PCT No.: PCT/KR2019/000955
§ 371 (c)(1),
(2) Date: Jul. 14, 2020

(87) PCT Pub. No.: WO2019/147013
PCT Pub. Date: Aug. 1, 2019

(65) Prior Publication Data
US 2021/0071166 A1 Mar. 11, 2021

(30) Foreign Application Priority Data
Jan. 24, 2018 (KR) .................. 10-2018-0008886

(51) Int. Cl.
C12N 15/10 (2006.01)
B01F 27/116 (2022.01)
(Continued)

(52) U.S. Cl.
CPC ........ C12N 15/1013 (2013.01); B01F 27/116 (2022.01); B01F 27/2122 (2022.01); B01F 27/213 (2022.01); B01F 27/806 (2022.01); B01F 31/445 (2022.01); B01F 31/70 (2022.01); B01F 33/5013 (2022.01);
(Continued)

(58) Field of Classification Search
CPC .. B01F 27/092; B01F 27/116; B01F 27/2122; B01F 27/213; B01F 27/25; B01F 27/806; B01F 31/445; B01F 31/70; B01F 33/5013; B01F 33/813; B01F 35/325; B01F 35/92; B01F 2035/99; B01F 2101/2204; B01F 2101/23; B01F 2101/44; B01L 3/0289; B01L 3/5085; B01L 2200/0657; B01L 2200/0668; B01L 2400/043; C12N 15/1013; C12Q 1/6806; G01N 2035/00534; B03C 1/28; C07K 1/145
See application file for complete search history.

(56) References Cited

FOREIGN PATENT DOCUMENTS

CN 205953992 U * 2/2017
KR 20090107927 A * 10/2009
(Continued)

OTHER PUBLICATIONS

English Translation of KR-20110131804-A (Year: 2011).*
(Continued)

Primary Examiner — Matthew D Krcha
Assistant Examiner — Austin Q Le
(74) Attorney, Agent, or Firm — Stein IP, LLC

(57) ABSTRACT

The present invention relates to a biological material extraction apparatus. According to the present invention, a tube in which a solution for use in extracting a biological material is contained is rotated to directly mix the solution, and cells where stirring is being conducted in each step are sealed to fundamentally block stirring-induced pollution between cells, thereby improving an extraction efficiency.

1 Claim, 13 Drawing Sheets

(51) Int. Cl.
  *B01F 27/2122* (2022.01)
  *B01F 27/213* (2022.01)
  *B01F 27/806* (2022.01)
  *B01F 31/00* (2022.01)
  *B01F 31/445* (2022.01)
  *B01F 33/501* (2022.01)
  *B01F 33/81* (2022.01)
  *B01F 35/32* (2022.01)
  *B01L 3/00* (2006.01)
  *C12Q 1/6806* (2018.01)
  *B01F 35/90* (2022.01)
  *B01F 35/92* (2022.01)
  *B01F 101/23* (2022.01)
  *B01F 101/44* (2022.01)

(52) U.S. Cl.
  CPC .......... *B01F 33/813* (2022.01); *B01F 35/325* (2022.01); *B01L 3/5085* (2013.01); *C12Q 1/6806* (2013.01); *B01F 35/92* (2022.01); *B01F 2035/99* (2022.01); *B01F 2101/23* (2022.01); *B01F 2101/44* (2022.01)

(56) References Cited

FOREIGN PATENT DOCUMENTS

| KR | 10-1025135 B1 | 3/2011 |
| KR | 10-2011-0131804 A | 12/2011 |
| KR | 10-1420094 B1 | 7/2014 |
| KR | 10-1653302 B1 | 9/2016 |
| KR | 20170120782 A * | 11/2017 |
| KR | 10-1813870 B1 | 1/2018 |
| KR | 10-1865615 B1 | 6/2018 |

OTHER PUBLICATIONS

English Translation of KR-101653302-B1 (Year: 2015).*
English Translation of KR-20090107927-A (Year: 2009).*
International Search Report dated Apr. 30, 2019, issued to International Application No. PCT/KR2019/000955.

* cited by examiner

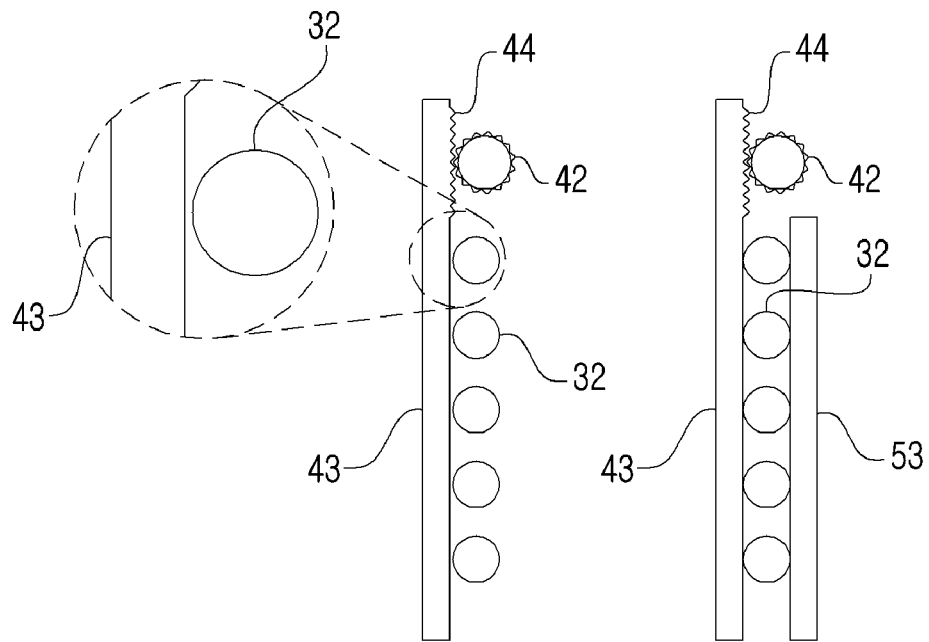
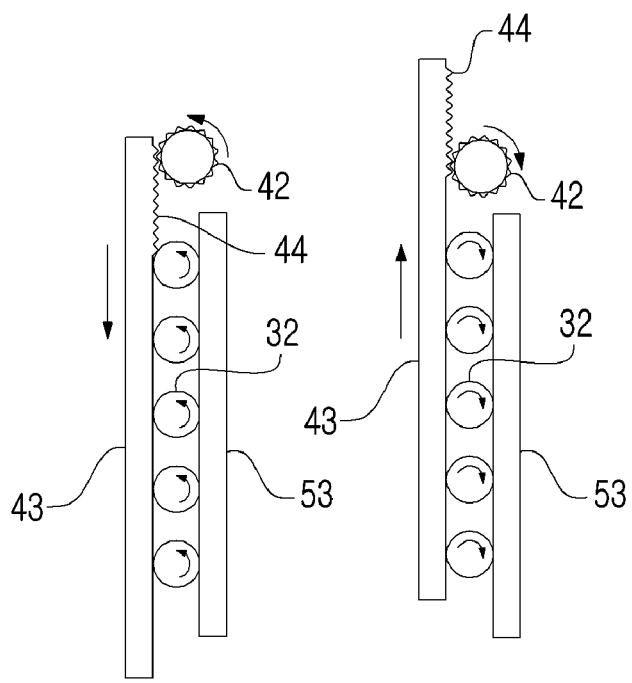
FIG. 5A  FIG. 5B
FIG. 5C  FIG. 5D

BIOLOGICAL MATERIAL EXTRACTION APPARATUS

CROSS-REFERENCE TO RELATED APPLICATIONS

This application is a national stage of International Application No. PCT/KR2019/000955, filed Jan. 23, 2019, which claims the benefit of Korean Application No. 10-2018-0008886, filed Jan. 24, 2018, in the Korean Intellectual Property Office. All disclosures of the documents named above are incorporated herein by reference.

TECHNICAL FIELD

The present invention relates to a biological material extraction apparatus, and more particularly, to technology for isolating and refining nucleic acid or biological materials from blood, cells or various biological samples.

BACKGROUND ART

To isolate and refine nucleic acid from blood or various biological samples becomes an important starting point in various fields, such as biology, biochemistry, molecular medicine, forensic medicine, diagnostic medicine, and so on. Recently, polymerase chain reaction (PCR) for DNA amplification is a necessary step frequently used in biological studies and diagnosis field, and requires isolation of nucleic acid from a biological sample.

Conventional methods for isolating nucleic acid have used harmful organic solvent such as phenol and chloroform. However, phenol and chloroform may have a bad influence on workers since being harmful chemical solvent.

Recently, methods for using materials with the property to bind with nucleic acid have been disclosed. There are silica, glass fiber, anion-exchange resin, deformed magnetic beads and the likes as such materials. Such materials do not use harmful organic solvents and minimize that nucleic acid is decomposed physically and biochemically in the isolation process. Moreover, fixed nucleic acid is less affected by a nucleic acid digesting enzyme.

However, such methods still have a disadvantage in that a worker has to use a pipette in order to move solid materials into another container one by one with the hand. Such work has a problem in that the worker may be exposed to latent viruses and germs from infected viruses and bacteria if the infected blood or bacteria are used as starting materials which have to isolate nucleic acid.

Korean Patent No. 10-1282841 (Jul. 1, 2013 entitled 'apparatus and method for isolating nucleic acid or biological materials', hereinafter called 'conventional art') discloses an apparatus for automatically carrying out the process of isolating biological materials from samples.

However, the conventional art uses a rack driving source which generates vibration in order to mix the samples, so it is difficult to mix the samples intensely.

DISCLOSURE

Technical Problem

Accordingly, the present invention has been made in an effort to solve the above-mentioned problems occurring in the prior arts, and it is an object of the present invention to provide a biological material extraction apparatus, which can directly mix a solution by rotating tubes contained in the solution used to extract biological materials in order to enhance extraction efficiency.

Technical Solution

To achieve the above objects, the present invention provides a biological material extraction apparatus including: a cassette seating part on which a cassette having a plurality of cells is seated; a cassette transferring part for transferring the cassette seating part; a tube support part located above the cassette seating part to support tubes inserted into the cells of the cassette; a tube lifting part for vertically lifting the tube support part; a magnet support part located above the tube support part to support magnets inserted into the tubes supported by the tube support part; a magnet lifting part for vertically lifting the magnet support part; and a tube rotating part for rotating the tubes when the tube support part lowers and the tubes are inserted into the cells of the cassette.

Here, the tube rotating part includes: a first motor for generating rotary power; a pinion gear interlocked with a rotary shaft of the first motor; and a first contact part getting in contact with the sides of the tubes and having a rack gear sawtooth-coupled with the pinion gear at a predetermined point.

Additionally, the biological material extraction apparatus further includes: a rotary support part getting in contact with the tubes to support the tubes at the opposite side of the first contact part when the first contact part of the tube rotating part gets in contact with the tubes, wherein the rotary support part includes: a second motor for generating rotary power; a support block linked with a rotary shaft of the second motor; and a second contact part disposed away from the rotational center of the support block to extend parallel to the direction of the rotary shaft of the support block.

Advantageous Effects

The biological material extraction apparatus according to the present invention can solve the problem that a worker is exposed to harmful materials during manual operation since mixing and cleaning of the solution and movement of beads are all automatically carried out.

Furthermore, the biological material extraction apparatus according to the present invention can greatly enhance extraction speed since simultaneously carrying out multiple sets of work using a plurality of tubes and magnets.

Additionally, the biological material extraction apparatus according to the present invention can show an intense mixing of the solution through a simple configuration since stirring the solution by rotating the tubes contained in the solution using the tube rotating part and the rotary support part.

Especially, the biological material extraction apparatus according to the present invention has a very simple mechanism for rotating the tubes. That is, in order to rotate the tubes, the biological material extraction apparatus has one tube rotating part having the first contact part as a driving means connected with the tubes. Because such a tube rotating part comes in contact only when rotation of the tubes is required, it is not needed that any structure to rotate the tubes is connected or combined with the tubes. That is, because there is no structure to be connected or combined for rotation of the tubes, there is no need to use exclusive tubes, so that tubes with various sizes and forms can be used without using any adapter.

In general, tubes are replaced with new ones every extraction work since being disposable. However, if a subsidiary unit for rotating the tubes must be connected or combined with the tubes every extraction work, a task setting process is very complicated and it takes a lot of time. However, the biological material extraction apparatus according to the present invention is rapid in initial setting work since there is no need to connect or combine a subsidiary unit with the tubes, and can reduce manufacturing costs of the extraction apparatus since the tube rotating part for rotating the tubes has the very simple structure.

DESCRIPTION OF DRAWINGS

FIGS. 5A-5D are conceptual diagrams showing a mechanism that tubes in the apparatus illustrated in FIG. 1 are rotated in a state where they get in contact with a first contact part and a second contact part.

EXPLANATION OF ESSENTIAL REFERENCE NUMERALS IN DRAWINGS

| 11 | main body | 12 | cover |
|---|---|---|---|
| 21 | magnet support part | 22 | magnet |
| 23 | magnet lifting part | 31 | tube support part |
| 32 | tube | 33 | tube lifting part |
| 40 | tube rotating part | 41 | first motor |
| 42 | pinion gear | 43 | first contact part |
| 44 | rack gear | 50 | rotary support part |
| 51 | second motor | 52 | support block |
| 53, 53' | second contact part | 54' | tube support groove |
| 61 | cassette seating part | 71 | cassette |
| 62 | cassette transferring part | 73 | solution |
| 63 | heating block | | |
| 72 | bead | | |

MODE FOR INVENTION

Hereinafter, reference will be now made in detail to the preferred embodiments of the present invention with reference to the attached drawings. However, some constructions regardless of the subject matter of the present invention may be omitted or condensed, but it doesn't mean that the omitted constructions are not needed in the present invention. Furthermore, the constructions may be combined to be used by those of ordinary skill in the art.

Figure 1:
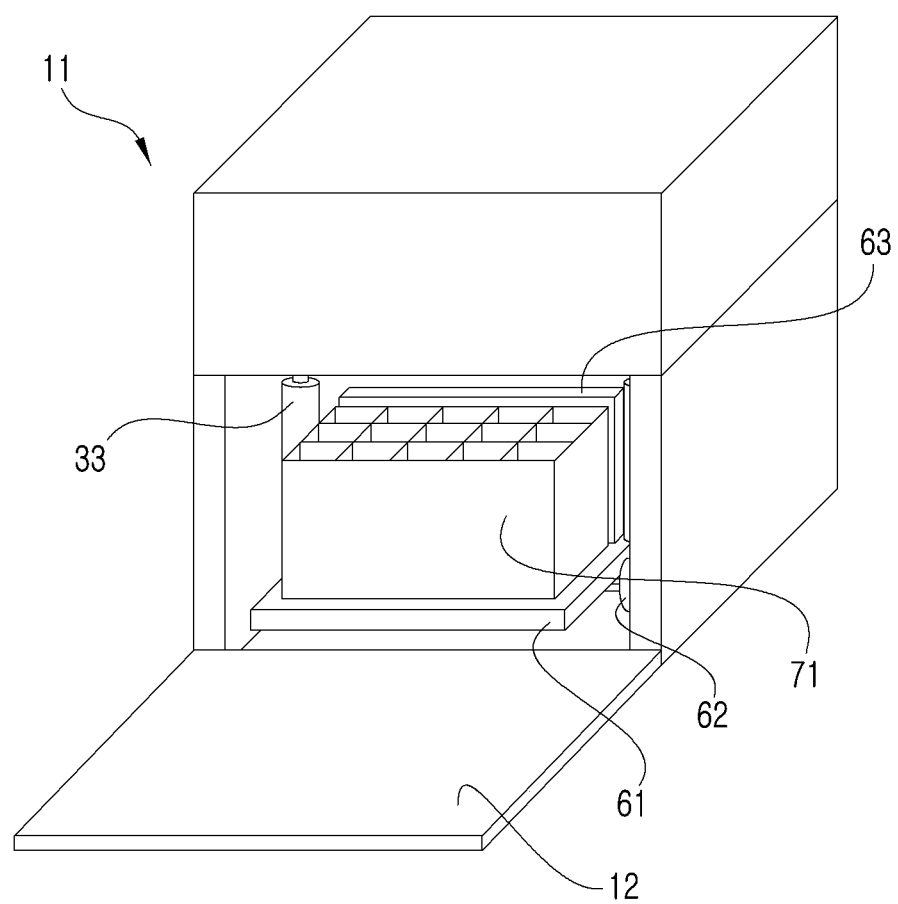
FIG. 1 is a perspective view showing a biological material extraction apparatus according to a first preferred embodiment of the present invention.
Figure 2:
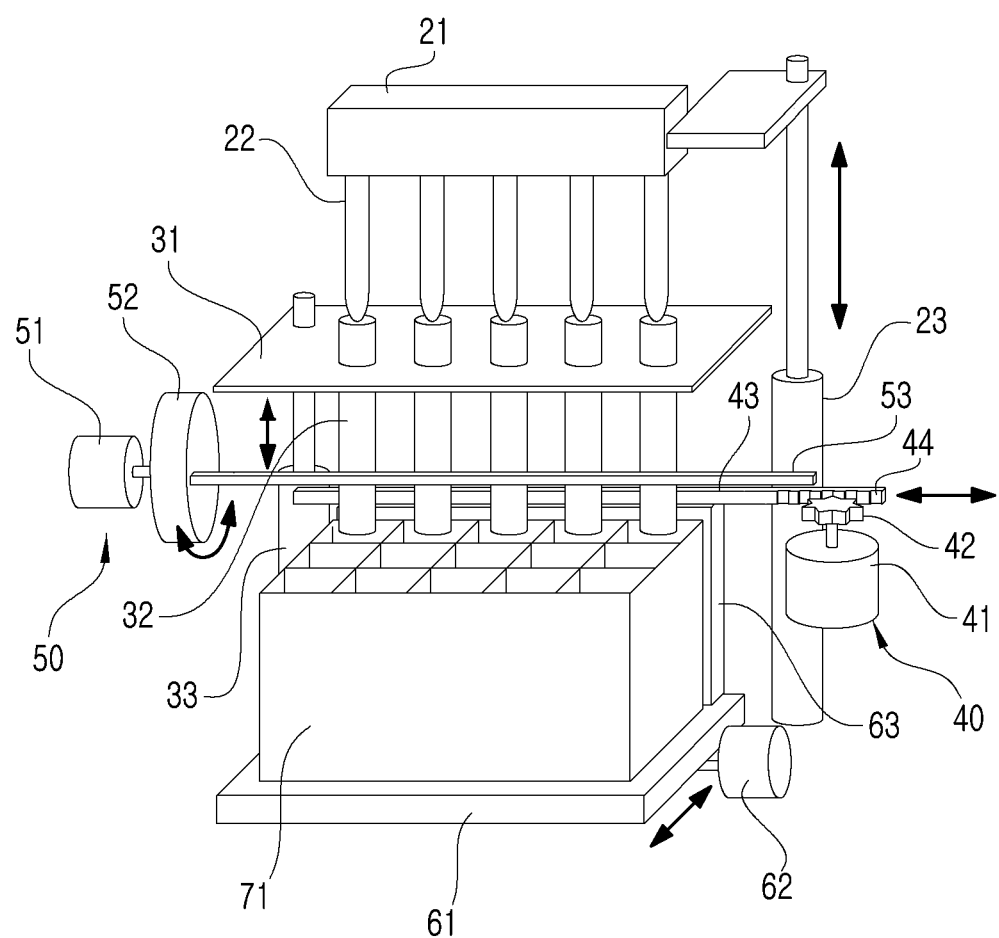
FIG. 2 is a perspective view showing an internal structure that a main body is removed from the biological material extraction apparatus illustrated in FIG. 1.

FIG. 1 is a perspective view showing a biological material extraction apparatus according to a first preferred embodiment of the present invention, and FIG. 2 is a perspective view showing an internal structure that a main body is removed from the biological material extraction apparatus illustrated in FIG. 1. As shown in FIGS. 1 and 2, the biological material extraction apparatus according to the first preferred embodiment of the present invention (hereinafter, called 'extraction apparatus' or 'apparatus' for the sake of convenient description) includes a main body 11, a cassette seating part 61, a cassette transferring part 62, a heating block 63, a tube support part 31, a tube lifting part 33, a magnet support part 21, magnets 22, a magnet lifting part 23, a tube rotating part 40, and a rotary support part 50.

The main body 11 having an internal space includes the other various components of the apparatus therein, and a cover 12 is disposed on the front face of the main body 11. Therefore, when a worker opens the cover 12 in order to draw out a cassette seating part 61, the worker can mount a cassette 71 and mount tubes 32 on a tube support part 31.

The cassette seating part 61 is mounted on the floor of the main body 11 to be movable in the back-and-forth direction. The cassette 71 has a plurality of cells and is seated on an upper portion of the cassette seating part 61. A solution 73 in which a sample, for instance, blood, a metallic or magnetic bead 72 of a metal material, and a binder are mixed is contained in each cell of the cassette 71.

A cassette transferring part 62 is to transfer the cassette seating part 61 in the back-and-forth direction. There may be various mechanisms to transfer the cassette seating part 61. However, in this embodiment, because the cassette transferring part 62 includes a motor and a pinion gear mounted on a motor shaft and a rack gear is formed on the bottom surface of the cassette seating part 61, the cassette seating part 61 is transferable in the back-and-forth direction depending on rotation power of the motor.

A heating block 63 is disposed on the upper portion of the cassette seating part 61 in order to supply heat to the solution 73 contained in the cassette 71. In more detail, the heating block 63 is mounted inside the cassette seating part 61, namely, on the rear surface of the main body 11. In some cases, the heating block 63 may be mounted below the cassette seating part 61.

The tube support part 31 and the magnet support part 21 are respectively disposed to support the tubes 32 and the magnets 22. Because a plurality of the tubes 32 and a plurality of the magnets 22 are arranged side by side, mixing and cleaning of the multiple sets of cells can be carried out at once.

First, the tube support part 31 is located on the upper portion of the cassette seating part 61, and has a plurality of through holes in which the tubes 32 are held vertically. There are various ways to hold the tubes 32 on the tube support part 31. For instance, the tubes 32 are designed to have the diameter slightly smaller than the diameter of the through holes, and each of the tubes 32 has a retaining jaw formed on the circumferential surface of the upper portion of the tube 32 so that each tube 32 is held on the tube support part 31 by the retaining jaw. Alternatively, if each of the tubes 32 is designed in such a way that the diameter of the lower portion is smaller than that of the upper portion, when the tube 32 is inserted down from above the through hole of the tube support part 31, the tube is held at the upper portion having the diameter larger than that of the through hole. Anyway, the tubes 32 must be able to do free rotation, namely, rotation of the tubes 32, in the state where the tubes 32 are held on the tube support part 31.

In the meantime, a predetermined point of the tube support part 31 is interlocked with the tube lifting part 33. Therefore, according to operation of the tube lifting part 33, the tube support part 31 and the tubes 32 held on the tube support part 31 are lifted vertically at the same time.

The magnet support part 21 is located above the tube support part 31, and the magnets 22 are respectively mounted at points corresponding to the tubes 32 held on the tube support part 31 located below. The magnets 22 may be detachably mounted on the magnet support part 21. Moreover, because a predetermined point of the magnet support part 21 is interlocked with the magnet lifting part 23, the magnet support part 21 and the magnets 22 are lifted vertically at the same time depending on operation of the magnet lifting part 23.

The tube rotating part 40 rotates the tubes 32 when the tubes 32 are inserted into the cells formed in the cassette 71 to intensely mix the solution 73. The tube rotating part 40 includes a first motor 41, a pinion gear 42, a first contact part 43, and a rack gear 44.

The first motor 41 for generating driving power is arranged in such a way that the direction of a rotary shaft is parallel to the longitudinal direction of the tubes 32, and the pinion gear 42 is mounted on the rotary shaft of the first motor 41. Furthermore, the first contact part 43 with a long bar shape gets in contact with the sides of the tubes 32, and the rack gear 44 which is sawtooth-coupled with the pinion gear 42 is formed at one side of the first contact part 43. Therefore, when the first motor 41 is rotated, the entire of the first contact part 43 is transferred in the longitudinal direction by the rack gear 44 interlocked with the pinion gear 42. In this instance, the first motor 41 may be a stepping motor of which a rotational direction is changed at predetermined time intervals. Therefore, the first contact part 43 is transferred in the longitudinal direction in a reciprocal manner by a reciprocating rotation of the first motor 41.

Here, in order to do the reciprocating transfer of the first contact part 43 in the longitudinal direction, a guide rail (not shown) for supporting the first contact part 43 and guiding a movement direction of the first contact part 43 must be disposed in the main body 11. However, because the structure of the guide rail is changeable in various ways according to designs by well-known skills, illustration and detailed description of the guide rail are omitted in this embodiment.

The first contact part 43 of the tube rotating part 40 reciprocates in the state where it gets in close contact with the sides of the tubes 32 held on the tube support part 31 side by side in order to rotate the tubes 32. However, if the first contact part 43 gets in close contact with only one side of each tube 32, the tubes 32 may not be rotated correctly due to weak adhesion. Moreover, because the tubes 32 are lifted and moved vertically to be perpendicular to the longitudinal direction of the first contact part 43, it is not supposed that the first contact part 43 always gets in contact with the tubes 32. That is, referring to FIG. 5A which is the conceptual diagram and a top view of the tubes 32 and the first contact part 43, the first contact part 43 is located on the sides of the tubes 32, but is slightly away from the tubes 32 at an initial position, so that the tubes 32 are not obstructed by contact with the first contact part 43 when moving vertically.

On the contrary, when it is necessary to rotate the tubes 32, the first contact part 43 must get in close contact with the tubes 32. As shown in FIG. 5B, the rotary support part 50 pushes and supports the tubes 32 at the opposite side of the first contact part 43, so that adhesion between the first contact part 43 and the tubes 32 is increased. The rotary support part 50 includes a second motor 51, a support block 52, and a second contact part 53.

The second motor 51 for generating rotary power is arranged in such a way that a direction of a rotary shaft is perpendicular to the longitudinal direction of the tubes 32, and the disc-shaped support block 52 is mounted at the rotary shaft of the second motor 51. Additionally, the second contact part 53 is disposed away from the rotational center of the support block 52 to extend parallel to the direction of the rotary shaft of the support block 52.

The second contact part 53 is disposed to bring the tubes 32 closer at the opposite side of the tubes 32 getting in contact with the first contact part 43. That is, in FIG. 2, the support block 52 is rotated by the driving power of the second motor 51 so that the second contact part 53 is spaced apart from the tubes 32. If the support block 52 is rotated in the opposite direction and the second contact part 53 comes in contact with the opposite sides of the tubes 32, the tubes 32 are stuck between the first contact part 43 and the second contact part 53 (see FIG. 5B). In this instance, when the second contact part 53 gets in contact with the tubes 32, the first contact part 43 and the second contact part 53 are located at the same height. Therefore, the first contact part 43 and the second contact part 53 located at the same height can press both sides of the tubes stably.

Therefore, in the above state, when the first motor 41 is operated so that the first contact part 43 moves horizontally, as shown in FIGS. 5C and 5D, the tubes 32 are rotated according to movement of the first contact part 43 in the state where they are supported by the second contact part 53. In the meantime, FIG. 3 is a schematically perspective view showing the state where the second contact part 53 gets in contact with the tubes 32 in the state where the tube support part 31 lowers and the tubes 32 are inserted into the cells of the cassette 71.

Now, a process of extracting biological materials using the biological material extraction apparatus illustrated in FIGS. 1 to 3 will be described as follows.

Figure 3:
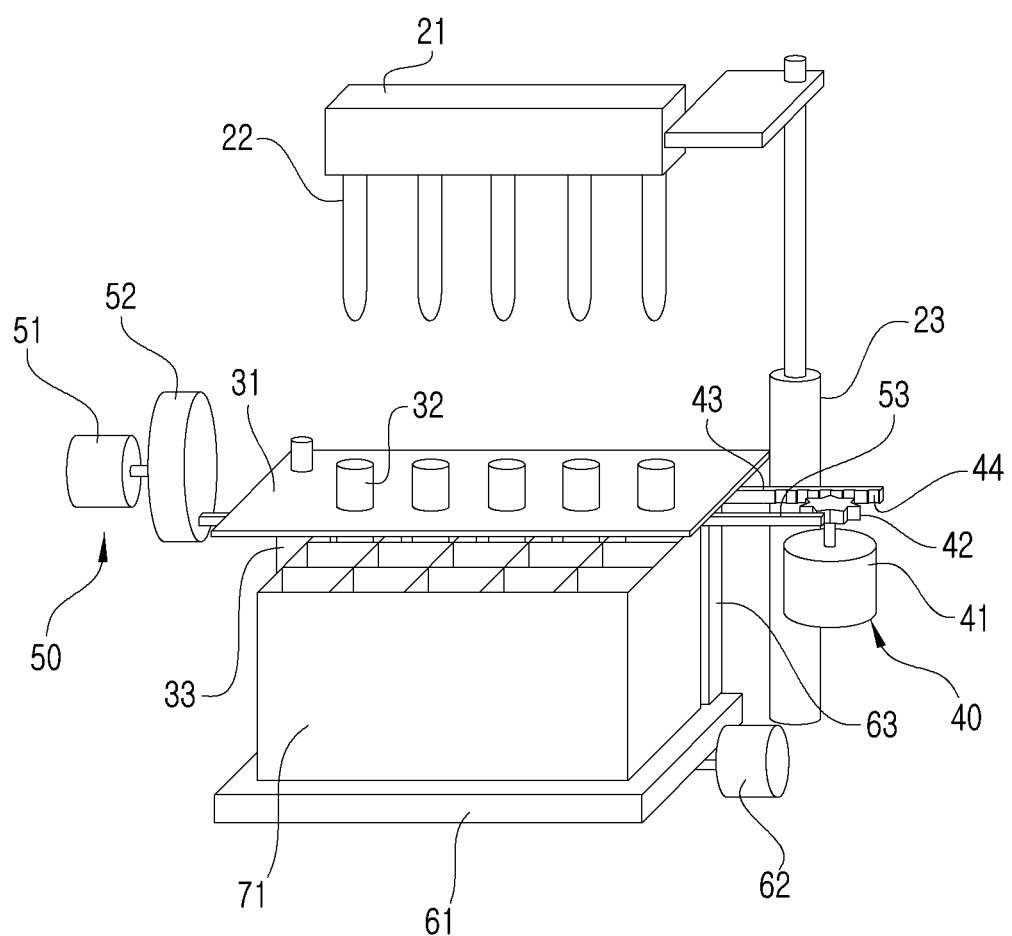
FIG. 3 is a view showing a state where tubes descend in the apparatus illustrated in FIG. 1.

FIGS. 4A-4F are views showing the process of extracting biological materials using the biological material extraction apparatus illustrated in FIGS. 1 to 3. That is, FIGS. 4A-4F are conceptual views showing a state where the cassette 71 and the tubes 32 are viewed from the support block 52 on the basis of FIGS. 2 and 3.

First, the worker prepares the cassette 71 in which the solution 73 is contained. The solution 73 contained in the cassette 71 may be mixture of a sample, beads 72 and a binder. After that, the worker opens the cover 12 disposed on the front surface of the main body 11 of the apparatus, and draws out the cassette seating part 61. After that, the worker mounts the cassette 71 on the cassette seating part 61. After that, the worker pushes the cassette seating part 61 into the main body 11. Of course, pushing and pulling of the cassette seating part 61 may be automatically carried out by the cassette transferring part 62.

Moreover, the tubes 32 are mounted on the tube support part 31. The tube support part 31 may be connected to the tube lifting part 33 so as to be drawn out when the cover 12 of the main body 11 is opened. As occasion demands, the tube support part 31 and the tube lifting part 33 are combined with each other to be detachable, so the tubes 32 are not mounted on the tube support part 31 but the entire of the tube support part 31 on which the tubes 32 are mounted is replaceable and the tube support part 31 is mounted on the tube lifting part 33.

After the tubes 32 and the cassette 71 are mounted, the worker closes the cover 12 and inputs an extraction start command through a command input unit disposed on the main body 11.

Figure 4A:
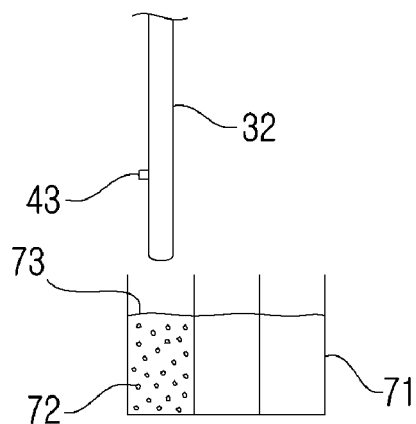
FIGS. 4A-4F are views showing an operational process of the biological material extraction apparatus illustrated in FIG. 1.
Figure 4B:
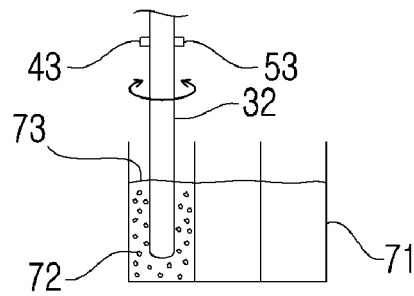

Referring to FIG. 4A, the first cell of the cassette 71 is located below the tube 32. After that, when the tube lifting part 33 is operated and the tube support part 31 and the tubes 32 lower together, as shown in FIG. 4B, the tubes 32 are contained in the solution 73.

Here, if both sides of the tubes 32 get in contact with the contact parts 43 and 53, the tubes 32 may not do the vertical movement smoothly. Therefore, when the vertical movement of the tubes 32 is needed, the second motor 51 rotates the support block 52, so that the second contact part 53 is separated from the tubes 32 as shown in FIGS. 2 and 5A. After that, when the tubes 32 lower, the second motor 51 operates the support block 52, and as shown in FIGS. 3, 4B and 5B, the second contact part 53 comes in contact with the tubes 32.

After that, when the first motor 41 is operated, driving power is transferred to the rack gear 44 interlocked with the pinion gear 42, so that the first contact part 43 does a reciprocating motion horizontally. In this instance, because the tubes 32 are stuck between the first contact part 43 and the second contact part 43, when the first contact part 43 moves horizontally, the tubes 32 are rotated by friction force of the first contact part 43. When the tubes 32 are rotated, the second contact part 53 firmly supports the tubes 32. Referring to FIGS. 5C and 5D, the first contact part 43 reciprocates horizontally according to rotation of the pinion gear 42, so that the tubes 32 are rotated in the state where they are supported by the second contact part 53.

Here, the first contact part 43 must push and rotate the tubes 32 with high friction force, and the second contact part 53 makes the tubes 32 do free rotation while supporting the tubes 32. Therefore, it is preferable that a material with high friction force, like rubber or silicon, be coated on the surface of the first contact part 43 getting in contact with the tubes 32, and it is also preferable that a slippery material be coated on the surface of the second contact part 53 getting in contact with the tubes 32. Because the tubes 32 is hindered from being rotated in position if friction force is high on the contact surfaces of the second contact part 53 and the tubes 32, it is good to make the tubes 32 rotated freely in position by the slippery contact surface of the second contact part 53.

Figure 6:
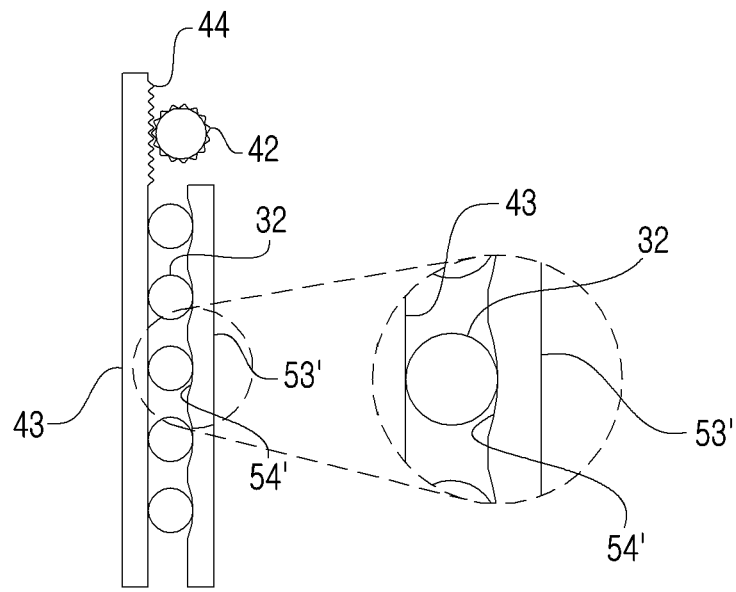
FIG. 6 is a view showing a state where a second contact part of another form is applied to the biological material extraction apparatus illustrated in FIG. 1.

In the meantime, the second contact part 53 pushes the tubes 32 toward the first contact part 43, and prevents the tubes 32 from moving horizontally when the first contact part 32 moves horizontally. For this, a second contact part 53' may be manufactured as shown in FIG. 6. That is, if a concave tube support groove 54' is formed at the point that the second contact part 53' gets in contact with the tubes 32, the tubes 32 is supported and rotated in more stably after being seated on the tube support groove 54'.

When the tubes 32 contained in the solution 73 are rotated while the first motor 41 rotates reciprocatingly during a predetermined period of time, the beads 72 contained in the solution 73 thresh so as to achieve mixing and cleaning for extracting biological materials.

Figure 4C:
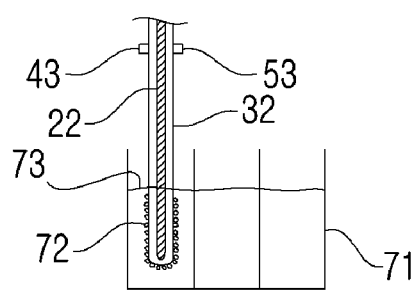
Figure 4D:
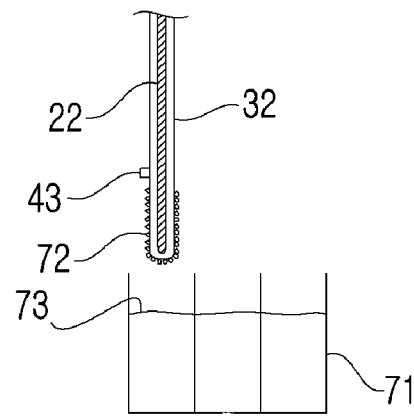

After stirring of the solution 73 according to the rotation of the tube 32 in the first cell is finished, the magnet lifting part 23 is operated so that the magnet support part 21 and the magnets 22 lower together, and as shown in FIG. 4C, the magnets 22 are inserted into the tubes 32. When the magnets 22 get to the bottoms of the tubes 32, the beads 72 contained in the solution 73 are adhered to the bottoms of the tubes 32 by magnetic force of the magnets 22. After that, as shown in FIG. 4D, the tube lifting part 33 and the magnet lifting part 23 simultaneously lift the tube support part 31 and the magnet support part 21. Therefore, even though the magnets 22 located in the tubes 32 are lifted and are exposed to the outside of the solution 73, the beads 72 are still adhered onto the bottom of the tubes 32.

Figure 4E:
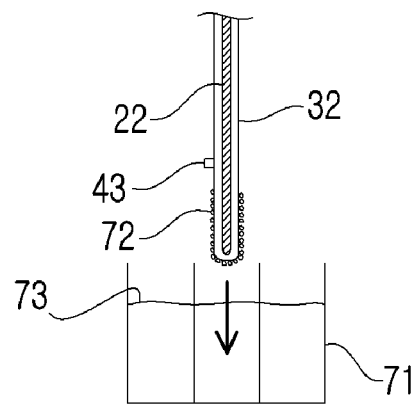

After that, the cassette transferring part 62 is operated to move the cassette seating part 61 and the cassette 71 horizontally. That is, as shown in FIG. 4E, the second cell of the cassette 71 is located at the bottom of the tube 32. In FIGS. 4A-4F, it seems that the tubes 32 and the magnets 22 are moved, but in fact, the cassette 71 is transferred. Of course, as occasion demands, the location of the cassette 71 may be fixed, and the tube lifting part 33 and the magnet lifting part 23 may be moved horizontally.

When the tube 32 on which the beads 72 are adhered is located in the next cell of the cassette 71, the tube lifting part 33 and the magnet lifting part 23 are operated at the same time, so that the tube 32 and the magnet 22 lower. Therefore, the bottom of the tube 32 on which the beads 72 are adhered is contained in the solution 73 which is contained in the next cell of the cassette 71. When the bottom of the tube 32 is contained in the solution 73 of the next cell is soaked, the tube 32 maintains its position and the magnet 22 is lifted. Therefore, the magnetic force applied to the beads 72 is removed, so that the beads 72 adhered on the bottom of the tube 32 drop down and are sunken in the solution 73.

Figure 4F:
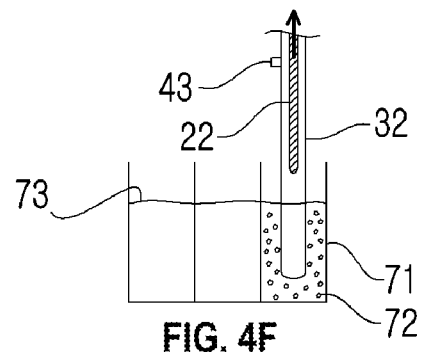

After that, the above-mentioned processes are repeated. That is, the first contact part 43 rotates the tubes 32 by operation of the first motor 41, mixing and cleaning in the solution 73 of the next cell are carried out again, and then, the magnets 22 enter into the tubes 32 so that the beads 72 are adhered on the bottom of the tubes 32. As shown in FIG. 4F, mixing and cleaning are repeated while moving to the next cell in sequence.

Because a plurality of the tubes 32 and a plurality of the magnets 22 are mounted on the tube support part 31 and the magnet support part 21, mixing and cleaning of multiple sets of cells can be simultaneously carried out in the cassette 71. The extraction processes using the extraction apparatus can be automatically carried out by a control program separately mounted.

As described above, the biological material extraction apparatus according to the present invention can solve the problem that the worker is exposed to harmful materials during manual operation since mixing and cleaning of the solution 73 and movement of the beads 72 are all carried out automatically.

Moreover, the biological material extraction apparatus according to the present invention can remarkably enhance extraction speed since the multiple sets of work can be carried out at the same time using a plurality of the tubes 32 and a plurality of the magnets 22.

Additionally, the biological material extraction apparatus according to the present invention can intensely mix the solution 73 using the simple structure since the solution 73 is stirred in the manner that the tubes 32 contained in the solution 73 are rotated through the tube rotating part 40 and the rotary support part 50.

Especially, the biological material extraction apparatus according to the present invention has the very simple mechanism to rotate the tubes 32. That is, the biological material extraction apparatus according to the present invention has just one tube rotating part 40 having the first contact part 43 as the driving means interlocked with the tubes 32 in order to rotate the tubes 32. Because the tube rotating part 30 gets in contact with the tubes 32 only when it is necessary to rotate the tubes 32, there is no need that any component to rotate tubes 32 is connected or combined with the tubes 32. That is, because there is no component to be connected or combined to rotate the tubes 32, there is no need to use exclusive tubes, so that tubes with various sizes and forms can be used without using any adapter.

That is, in general, tubes are replaced with new ones every extraction work since being disposable. However, if a subsidiary unit for rotating the tubes must be connected or combined with the tubes every extraction work, a task setting process is very complicated and it takes a lot of time. However, the biological material extraction apparatus according to the present invention is rapid in initial setting work since there is no need to connect or combine a subsidiary unit with the tubes, and can reduce manufacturing costs of the extraction apparatus since the tube rotating part for rotating the tubes has the very simple structure.

Till now, referring to FIGS. 1 to 6, the structure and the operational process of the biological material extraction apparatus are described. FIGS. 1 to 6 show an example of the biological material extraction apparatus to stir the solution by rotating the tubes. That is, because the idea of the present invention is to stir the solution in the tube rotation manner, various modifications may be derived besides the above example illustrated in FIGS. 1 to 6. Hereinafter, a biological material extraction apparatus to which a tube rotation mechanism of another way is applied will be described.

Figure 7:
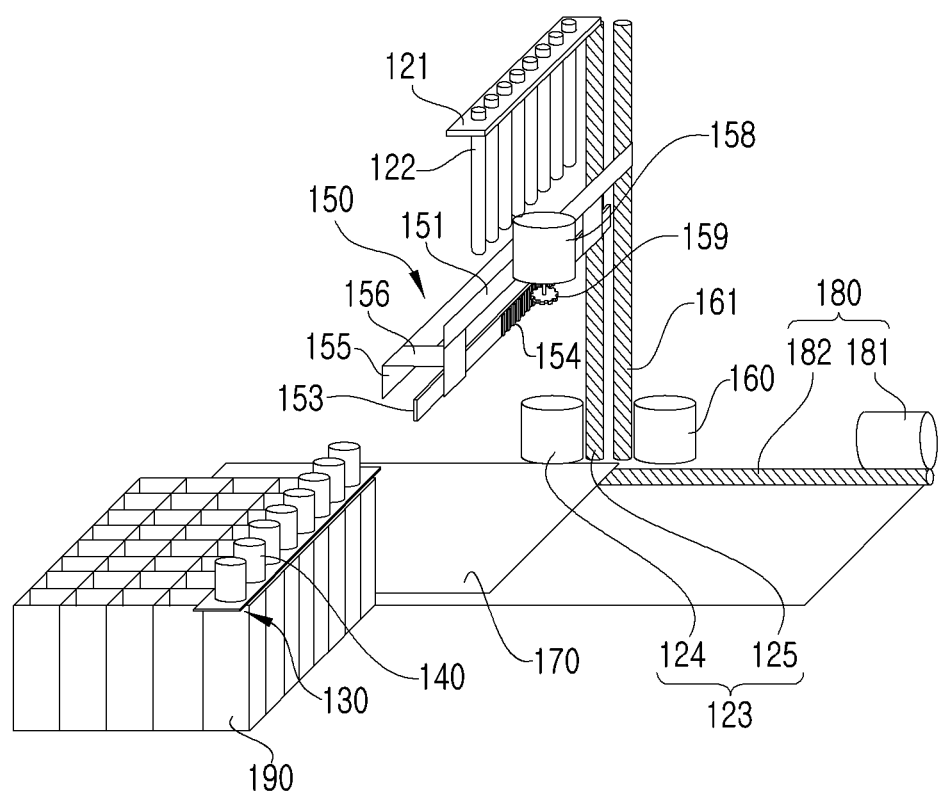
FIG. 7 is a conceptual diagram showing a biological material extraction apparatus according to a second preferred embodiment of the present invention.
Figure 8A:
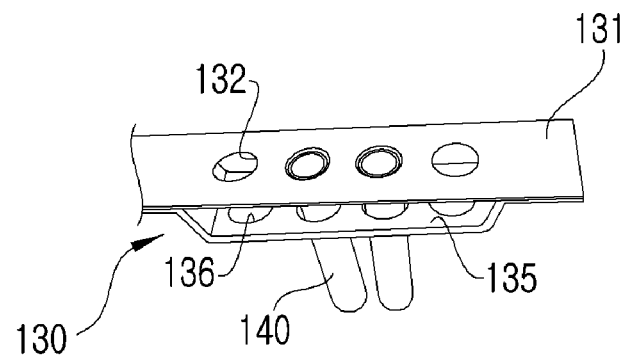
FIGS. 8A and 8B are views showing a tube support part in the biological material extraction apparatus illustrated in FIG. 7.
Figure 8B:
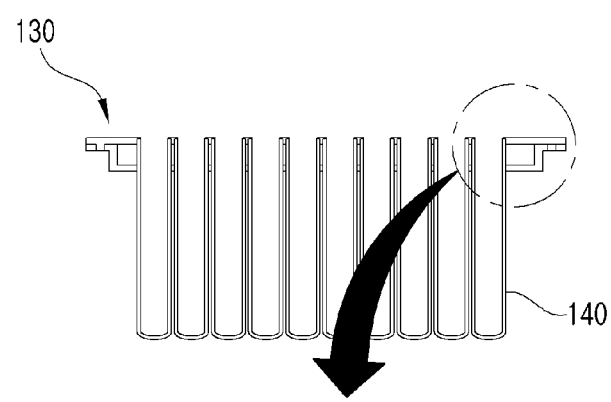
Figure 8B:
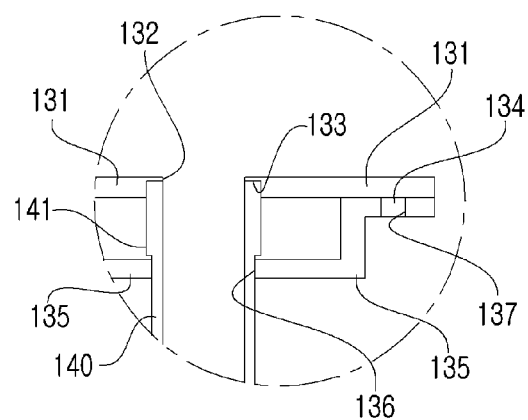
Figure 9A:
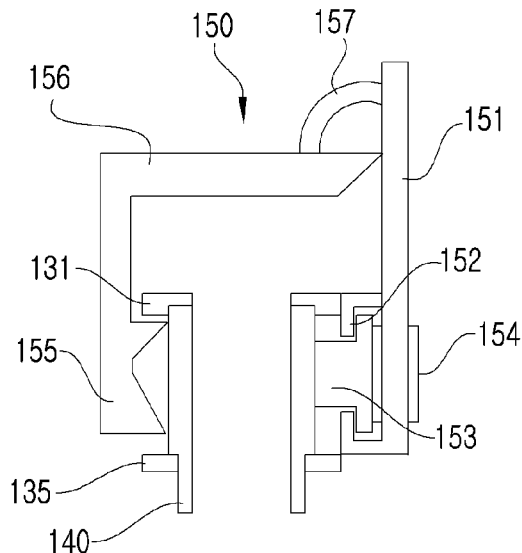
FIGS. 9A and 9B are views showing a state where the tube support part is mounted on a tube rotating part in the apparatus illustrated in FIG. 7.
Figure 9B:
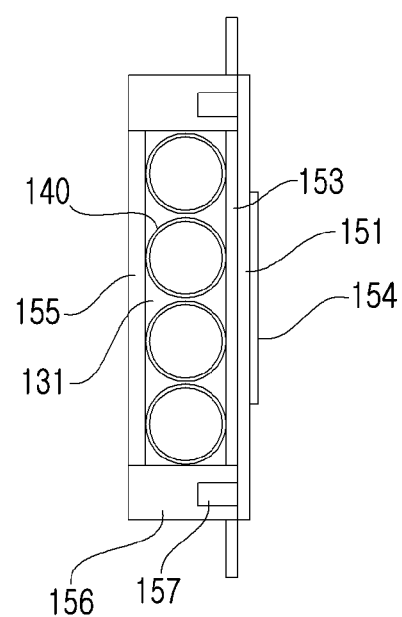

FIG. 7 is a conceptual diagram showing a biological material extraction apparatus according to a second preferred embodiment of the present invention, FIGS. 8A-8B are views showing a tube support part in the biological material extraction apparatus illustrated in FIG. 7, and FIGS. 9A-9B are views showing a state where the tube support part is mounted on a tube rotating part in the apparatus illustrated in FIG. 7.

As shown in FIGS. 7 to 9B, the biological material extraction apparatus according to the second preferred embodiment of the present invention includes a cassette seating part 170, a cassette transferring part 180, a tube support part 130, a tube rotating part 150, a magnet support part 121, magnets 122, and a magnet lifting part 123. Of course, the biological material extraction apparatus according to the second preferred embodiment of the present invention may further include the main body and the cover, but the main body and the cover are omitted in the drawings.

The cassette seating part 170 is to support a cassette 190 having a plurality of cells, and a heating block for supplying heat to a solution 73 contained in the cassette 190 is disposed integrally with the cassette seating part 170. Moreover, the cassette seating part 170 is mounted to be horizontally movable by the cassette transferring part 180. The cassette transferring part 180 for transferring the cassette seating part 170 may be designed in various ways, but in this embodiment, the cassette seating part 170 is transferred by operation of a cassette transfer motor 181 and a cassette transfer screw 182. That is, because one side of the cassette seating part 170 is interlocked with the cassette transfer screw 182, when the cassette transfer screw 182 is rotated by operation of the cassette transfer motor 181, the cassette seating part 170 and the cassette 190 seated on the cassette seating part 170 are moved horizontally.

The tube support part 130 is to support the tubes 140. FIG. 8A is a perspective view showing the tube support part 130 on which the tubes 140 are mounted, and FIG. 8B is a schematically sectional view of the tube support part 130. The tube support part 130 of FIG. 8A can support up to four tubes 140, and the tube support part 130 of FIG. 8B can support up to ten tubes 140. However, the number of the tubes supported by the tube support par 130 can be changed by a design change according to a length extension of the tube support part 130, and its basic structure is the same.

As shown in FIGS. 8A-8B, the tube support part 130 includes an upper support part 131 and a lower support part 135. The upper support part 131 has upper holes 132 formed such that the magnets 122 can enter into the open upper portions of the tubes 140, and an upper jaw 133 is formed on the bottom surface of the circumference of each upper hole 132. Moreover, lower holes 136 through which the tubes 140 pass are formed in the lower support part 135.

The upper holes 132 of the upper support part 131 and the lower holes 136 of the lower support part 135 are formed to correspond to each other when the upper support part 131 and the lower support part 135 are combined with each other. Furthermore, fitting protrusions 134 which protrude downwards are formed at both sides of the upper support part 131, and fitting holes 137 to which the fitting protrusions 134 of the upper support part 131 are inserted are formed at both sides of the lower support part 135.

In the meantime, the tubes 140 have retaining jaws 141 respectively formed at the upper circumference to protrude outwards. When the tubes 140 are mounted on the tube support part 130, first, in the state where the upper support part 131 and the lower support part 135 are separated, the tubes 140 are inserted into the lower holes 136 of the lower support part 135. After that, when the fitting protrusions 134 of the upper support part 131 are inserted and fixed into the fitting holes 137 of the lower support part 135, the upper support part 131 and the lower support part 135 are firmly fixed, and the retaining jaws 141 of the tubes 140 are caught to the circumferences of the lower holes 136 of the lower support part 135 not to slip down. Additionally, because the upper portions of the retaining jaws 141 of the tubes 140 are caught to the upper jaws 133 of the upper support part 131, even though power acts upwards from the bottom of the tubes 140, the tubes 140 do not go upwards.

The tube rotating part 150 vertically lifts the tube support part 130 and the tubes 140 according to the extraction process or rotates each of the tubes 140 while supporting the tubes 140, in more detail and supporting the tube support part 130 on which the tubes 140 are mounted.

FIG. 9A is a conceptual diagram and a side elevation view showing the state where the tube support part 130 is mounted on the tube rotating part 150, and FIG. 9B is a conceptual diagram viewed from the top. As shown in FIGS. 7 and 9A-9B, the tube rotating part 150 includes a base part 151, a first contact part 153, a second contact part 155, an extension part 156, an elastic member 157, a first motor 158, and tube lifting parts 160 and 161.

The base part 151 has a length that the tubes 140 correspond to the direction that the tubes 140 are arranged on the tube support part 130, and supports other components of the tube rotating part 150. Moreover, one side of the base part 151 is connected to the tube lifting screws 161 of the tube lifting parts 160 and 161. Furthermore, a guide 152 is disposed at a lower portion of one side of the base part 151, and the first contact part 153 is mounted on the guide 152 to be horizontally movable.

The first contact part 153 moves horizontally while getting in contact with the tubes 140 so as to rotate the tubes 140. The one side of the first contact part 153 is flat, but gets in contact with the tubes 140 since being made of a material with high friction force. The rack gear 154 is formed at the other side of the first contact part 153. Therefore, when the first motor 158 is operated and the pinion gear 159 is rotated, the first contact part 153 moves horizontally by interlock of the pinion gear 159 and the rack gear 154.

The second contact part 155 is mounted to be parallel to the first contact part 153 at a predetermined interval, the first contact part 153 gets in contact with the opposite sides of the tubes 140 to support the tubes 140. The second contact part 155 is connected with the base part 151 by the extension part 156. In more detail, the extension part 156 connects both ends of the base part 151 and the second contact part 155 with each other. Therefore, an exposure space is formed between both sides of the extension part 156 so that the magnets 122 can enter into the space.

Additionally, portions where the extension part 156 and the base part 151 are connected are connected to be rotatable at a predetermined angle, and the extension part 156 and the base part 151 are connected through the elastic member 157. The elastic member 157 provides elastic force so that the second contact part 155 applies power toward the first contact part 153.

The tube lifting parts 160 and 161 are to vertically lift the tube rotating part 150 and the tube support part 130. The tube lifting parts 160 and 161 include the tube lifting motor 160 and the tube lifting screw 161. That is, because a certain point of the base part 151 is linked with the tube lifting screw 161, when the tube lifting screw 161 is rotated by operation of the tube lifting motor 160, the base part 151 is lifted vertically, and the first contact part 153, the second contact part 155 and the tube support part 130 connected to the base part 151 are lifted vertically.

The magnet support part 121 is to support the magnets 122 mounted corresponding to the positions of the tubes 140, the magnet support part 121 is moved vertically in link with the magnet lifting part 123. The magnet lifting part 123 includes a magnet lifting motor 124 and a magnet lifting screw 125, and the magnet support part 121 is lifted by operation of the magnet lifting motor 124 since the magnet support part 121 is interlocked with the magnet lifting screw 125.

Hereinafter, referring to FIGS. 7 to 9B, a process of extracting biological materials using the biological material extraction apparatus according to the second embodiment of the present invention will be described.

First, the worker prepares a cassette 190 in which a solution 73 is contained. After that, the worker separates the lower support part 135 from the upper support part 131 of the tube support part 130, inserts the tubes 140 into the lower holes 136 of the lower support part 135, and inserts the fitting protrusions 134 of the upper support part 131 into the fitting holes 137 of the lower support part 135 to prepare sets of the tubes. Therefore, the lower portions of the retaining jaws 141 protruding from the upper circumferences of the tubes 140 are respectively caught to the circumferences of the lower holes 136 so as not to slip down, and the upper portions of the retaining jaws 141 are caught to the upper jaws 133 of the upper support part 131 not to go upwards. In addition, the open upper portions of the tubes 140 are exposed out through the upper holes 132 of the upper support part 131. As occasion demands, sets of the tubes that the tubes 140 are combined with the tube support part 130 may be prepared in a previously packed state.

After that, the sets of the tubes enter into the first cell 140 from above the cassette 190 so that the lower portions of the tubes 140 are inserted into the first cell of the cassette 190. When the cassette 190 on which the sets of the tubes are seated is prepared, the worker opens the cover of the main body and puts the cassette 190 on the cassette seating part 170.

Here, when the cassette 190 is put on the cassette seating part 170, the cassette 190 enters in the direction to correspond to the longitudinal direction of the tube support part 130, so that the tube support part 130 put on the cassette 190 is naturally combined with the tube rotating part 150.

That is, when the cassette 190 is put on the cassette seating part 170, the tube rotating part 150 lowers down. Moreover, an interval between the second contact part 155 and the first contact part 153 is slightly smaller than the outer diameter of the tube 140. In this instance, when the worker pushes the cassette 190 into the cassette seating part 170, one end of the tube support part 130 seated in the first cell of the cassette 190 enters into a space between the first contact part 153 and the second contact part 155.

After the tube support part 155 completely enters into the space between the first contact part 153 and the second contact part 155, namely, into the space which is smaller than the outer diameter of the tube 140, the tube 140 gets in contact between the second contact part 155 and the first contact part 153 by elastic force of the elastic member 157. Therefore, as shown in FIG. 9A, the upper support part 131 and the lower support part 135 of the tube support part 130 are respectively located above and below the first contact part 153 and the second contact part 155, and both sides of the tubes 140 seated on the tube support part 130 are compressed by the first contact part 153 and the second contact part 155.

After that, when a control command is inputted, the extraction apparatus starts the extraction process. First, the tubes 140 are inserted into the first cell of the cassette 190, and the tubes 140 are fit between the contact parts 153 and 155 of the tube rotating part 150. In this state, when the pinion gear 159 is rotated while the first motor 158 is operated, driving power is transferred to the rack gear 154 linked with the pinion gear 159, so that the first contact part 153 carries out a horizontal reciprocating motion. In this instance, because the tubes 140 are fit between the first contact part 153 and the second contact part 155, when the first contact part moves horizontally, the tubes 140 are rotated by friction force of the first contact part 153. When the tubes 140 are rotated, the second contact part 155 firmly supports the tubes 140 at the opposite side.

Here, because the first contact part 153 must rotate the tubes 140 with high friction force and the second contact part 155 must make the tubes 140 rotated freely in the supported state, it is preferable that the surface of the first contact part 153 which gets in contact with the tubes 140 be coated with a material with high friction force, such as rubber or silicon, and the surface of the second contact part 155 which gets in contact with the tubes 140 be coated with a slippery material.

When the tubes 140 contained in the solution 73 are rotated while the first motor 158 reciprocatingly rotates during a predetermined period of time, the beads 72 contained in the solution 73 thresh so as to carry out mixing and cleaning for extraction of the biological materials. In this instance, while stirring the solution 73, the solution 73 located in a specific cell runs over to the neighboring cell, and it may pollute the solution 73 in another cell. That is, because the tubes 140 are inserted in the solution 73 of the cell in which stirring is being carried out, the water level rises as high as the number of the inserted tubes 140, and the solution 73 may run over through the cell upper end portion while threshing according to the intense rotation of the tubes 140.

However, in the present invention, when the tubes 140 are rotated and the solution 73 is stirred, the tube support part 130 is combined with the upper portions of the tubes 140, and the lower support part 135 of the tube support part 130 covers and seals the open upper portion of the corresponding cell. Therefore, even though the solution 73 runs over the cell while threshing, because the lower support part 130 perfectly blocks the open upper portion of the cell, it can perfectly prevent that the solution of the corresponding cell runs over toward the neighboring cell and pollutes the solution of the neighboring cell.

Moreover, as described above, after the sets of the tubes are seated in the first cell of the cassette 190, namely, the sets that the tubes 140 are combined with the tube support part 130, the cassette 190 is pushed into the cassette seating part 170. Also in this instance, because the water level in the first cell in which the tubes 140 are inserted rises as high as the number of the inserted tubes 140, the solution may run over while the cassette 190 enters. However, even in this instance, because the lower support part 135 of the tube support part 130 seals the open end portion of the upper portion of the cell, it can solve the problem that the solution runs over and pollutes the solution in another cell during a mounting process.

After stirring of the solution 73 is achieved according to rotation of the tubes 140 in the first cell, the magnet lifting part 123 is operated to lower the magnet support part 121 and the magnets 122, and the magnets 122 enter into the tubes 140. When the magnets 122 enters to the bottoms of the tubes 140, the beads 72 contained in the solution 73 are stuck to the bottom of the tubes 140 by magnetic force of the magnets 122. After that, the tube lifting motor 160 and the magnet lifting motor 124 are operated at the same time to rise the tubes 140 and the magnets 122 at the same time. Therefore, even though the magnets 122 located in the tubes 140 are lifted together with the tubes 140 and are exposed out of the solution 73, the beads 72 are still stuck to the bottoms of the tubes 140.

After that, the cassette transferring part 180 is operated to horizontally move the cassette seating part 170 and the cassette 190 so that the second cell of the cassette 190 is located below the tubes 140. When the tubes 140 to which the beads 72 are stuck are located at the position of the next cell of the cassette 190, the tubes 140 and the magnets 122 lower down at the same time, and then, the tubes 140 are maintained in the state where they are put in the solution 73, and only the magnets 122 rise. Therefore, the magnetic force applied to the beads 72 is removed, and the beads 72 attached to the bottoms of the tubes 140 drop down, and are put in the solution 73 contained in the second cell of the cassette 190.

After that, the above-mentioned process is repeated, so that mixing and cleaning are repeated while the beads 72 are moved to the cells of the cassette 190 in sequence.

Figure 10:
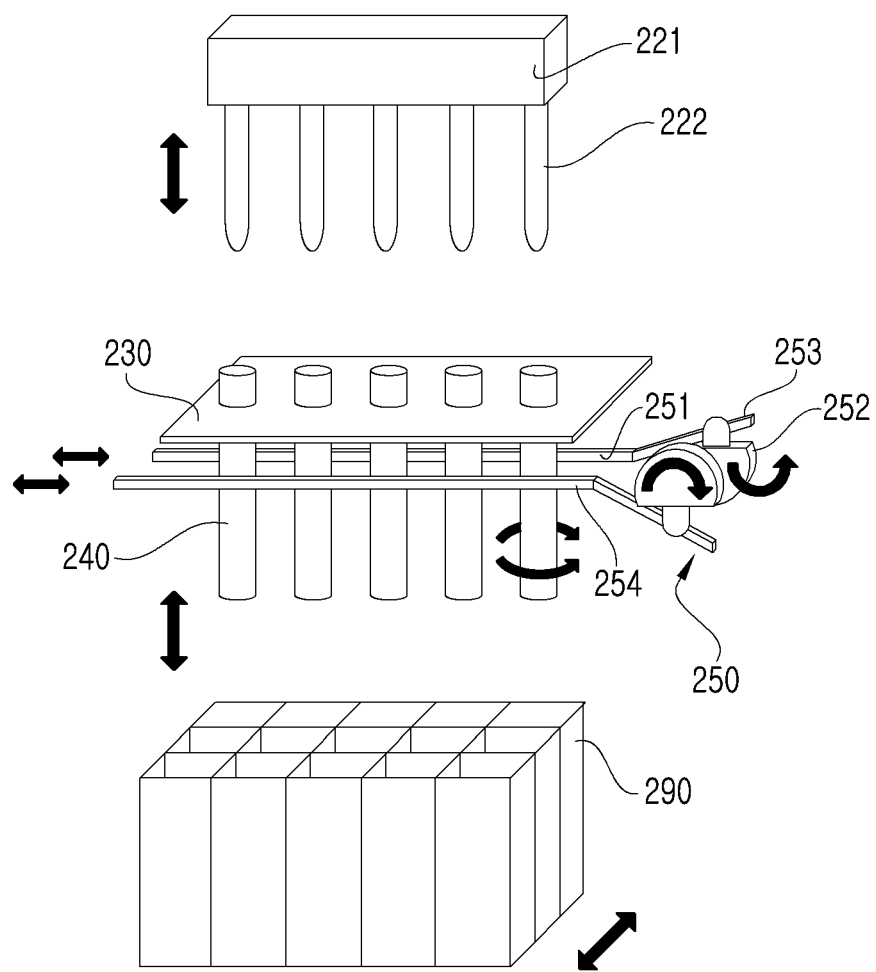
FIGS. 10 to 14 are conceptual diagrams showing a biological material extraction apparatus according to further preferred embodiments of the present invention.

FIG. 10 is a conceptual diagram showing a biological material extraction apparatus according to a third preferred embodiment of the present invention. The extraction apparatus illustrated in FIG. 10 includes a magnet support part 221, magnets 222, a tube support part 230, and a tube rotating part 250. Moreover, the extraction apparatus illustrated in FIG. 10 may further include a magnet lifting part for lifting the magnet support part 221, a tube lifting part for lifting the tube support part 230, a cassette transferring part for horizontally moving the cassette 290, and a heating block, but they are not shown in the drawings. However, the magnet lifting part, the tube lifting part and the cassette transferring part can be sufficiently inferred through the above-mentioned examples referring to FIGS. 1 to 9B. That is, the principle to move or lift horizontally by a cylinder driving method or a screw driving method can be applied to this embodiment of the present invention.

The tube rotating part 250 illustrated in FIG. 10 is different from that of the previous embodiments in that the tube rotating part 250 rotates the tubes 240 by operation of a crank 252 and a connecting rod 253. That is, the tube rotating part 250 includes a first contact part 251, a second contact part 254, a crank 252, and a connecting rod 253.

The first contact part 251 and the second contact part 254 get in contact with both sides of the tubes 240, and one side of each contact part is connected with one side of each connecting rod 253. Moreover, the other side of the connecting rod 253 is connected to the crank 252 to transfer driving power according to operation of the crank 252.

In this embodiment, the crank 252 transfers reciprocating driving power to the connecting rod 253, and the contact parts 251 and 254 carry out a horizontally reciprocating motion, so that the tubes 240 located between the contact parts 251 and 254 are rotated. Not shown in the drawings, but the contact parts 251 and 254 are supported by a guide to do a horizontal movement only in a predetermined area.

Figure 11:
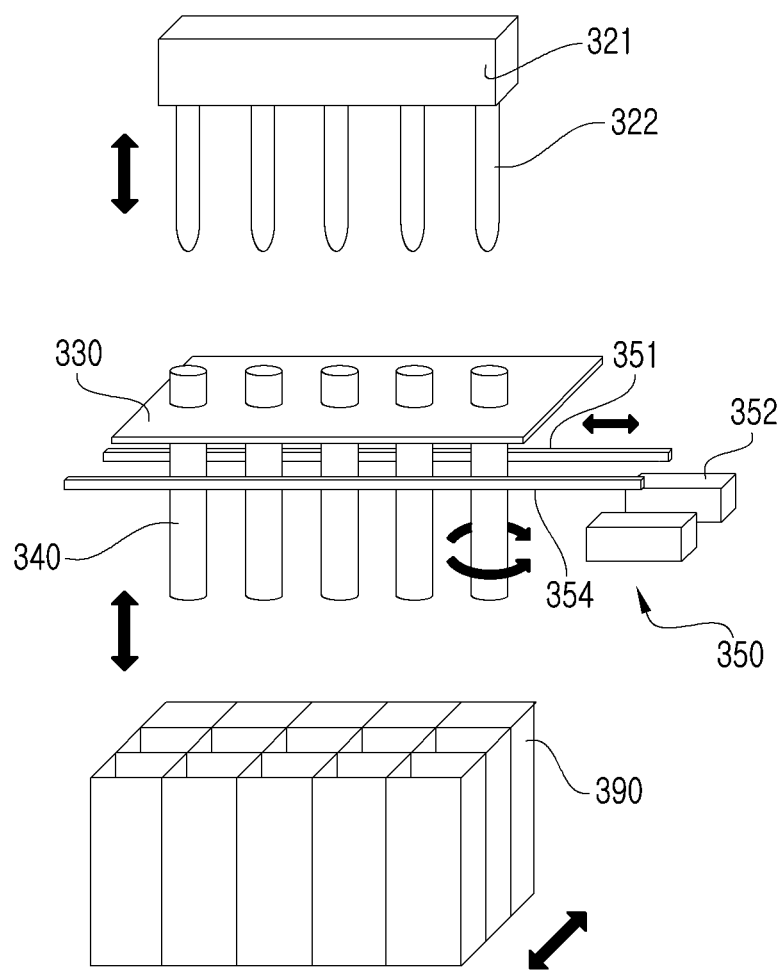

FIG. 11 is a conceptual diagram showing a biological material extraction apparatus according to a fourth preferred embodiment of the present invention. The extraction apparatus illustrated in FIG. 11 includes a magnet support part 321, magnets 322, a tube support part 330, and a tube rotating part 350. The extraction apparatus illustrated in FIG. 11 may further include components for horizontally moving and lifting the magnet support part 321, the tube support part 330 and a cassette 390. However, the fourth embodiment is different from the above embodiments in the structure of the tube rotating part 350 for rotating the tubes 340.

The tube rotating part 350 includes a first contact part 351, a second contact part 354, and electromagnets 352. The first contact part 351 and the second contact part 354 get in contact with both sides of the tubes 340, and a permanent magnet is mounted at one side of each of the contact parts 351 and 354, and the electromagnets 352 are mounted adjacent to the position where the permanent magnets are mounted. Therefore, when polarity of the electromagnets 352 is changed in sequence by operation of a control unit (not shown), the contact parts 351 and 354 are pushed or pulled according to phases with the polarity of the permanent magnets mounted on the contact parts 351 and 354, so that the entire of the contact parts 351 and 354 can be moved horizontally. Therefore, the tubes 340 are rotated according to the horizontal movement of the contact parts 351 and 354.

Figure 12:
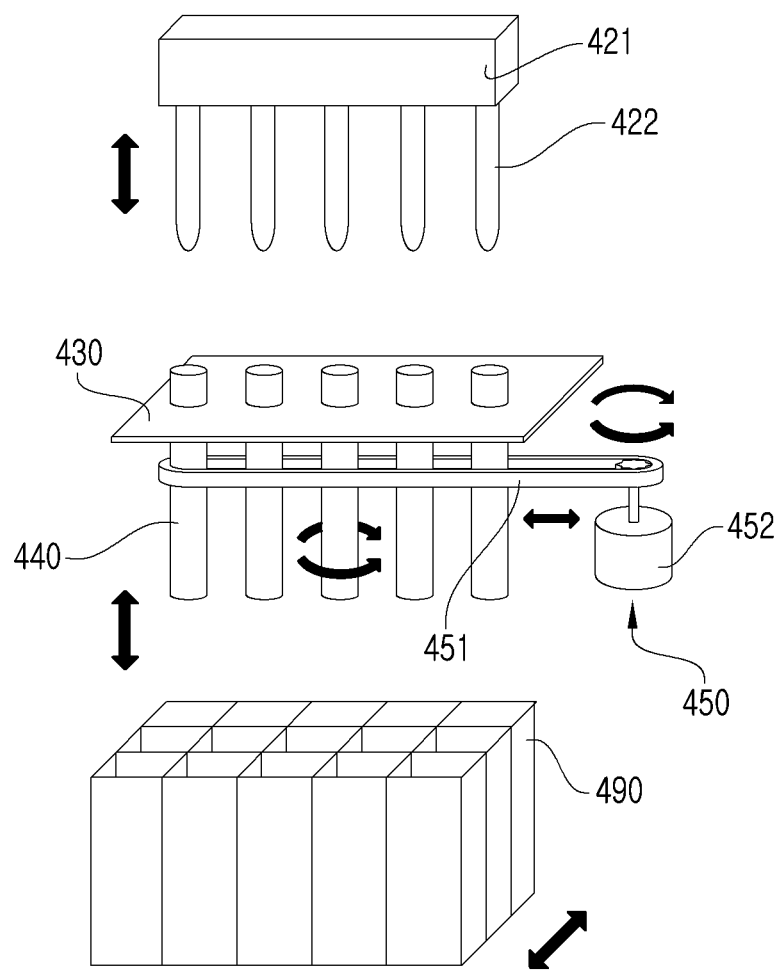

FIG. 12 is a conceptual diagram showing a biological material extraction apparatus according to a fifth preferred embodiment of the present invention. The extraction apparatus illustrated in FIG. 12 includes a magnet support part 421, magnets 422, a tube support part 430, and a tube rotating part 450. The extraction apparatus illustrated in FIG. 12 may further include components for horizontally moving and lifting the magnet support part 421, the tube support part 430 and a cassette 490. However, the fifth embodiment is different from the above embodiments in the structure of the tube rotating part 450 for rotating the tubes 440.

The tube rotating part 450 includes a belt 451 and a belt driving motor 452. The belt driving motor 452 is linked with one side of the belt 451, and the tubes 440 are located inside at the other side of the belt 451. A contact means (not shown) may be further mounted at both sides of the belt 451 where the tubes 440 are located, in order to apply power from the outside to the inside so that the belt 451 and the tubes 440 can come in closer contact with each other and in order not to have any influence on rotation of the belt 451.

Therefore, when the belt driving motor 452 is operated and the belt 451 is rotated, the tubes 440 getting in contact with the belt 451 can rotate in a lump inside the belt 451.

Figure 13:
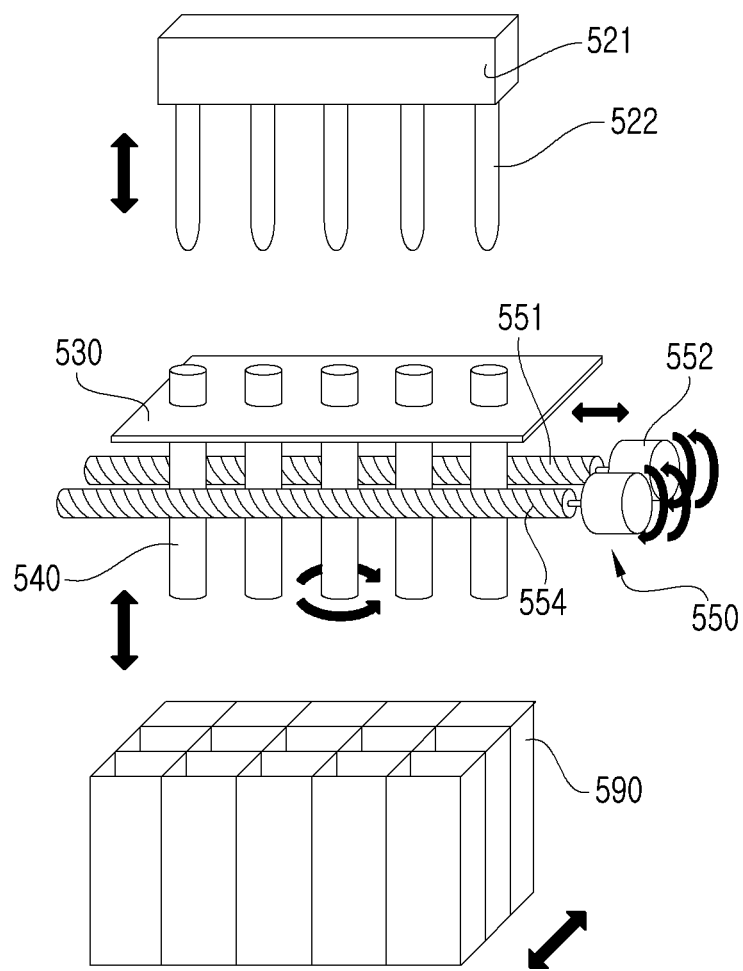

FIG. 13 is a conceptual diagram showing a biological material extraction apparatus according to a sixth preferred embodiment of the present invention. The extraction apparatus illustrated in FIG. 13 includes a magnet support part 521, magnets 522, a tube support part 530, and a tube rotating part 550. The extraction apparatus illustrated in FIG. 13 may further include components for horizontally moving and lifting the magnet support part 521, the tube support part 530 and a cassette 590. However, the sixth embodiment is different from the above embodiments in the structure of the tube rotating part 550 for rotating the tubes 540.

The tube rotating part 550 includes a first contact screw 551, a second contact screw 554, and a contact screw driving motor 552. The first contact screw 551 and the second contact screw 554 respectively have screw threads, and both sides of the tubes 540 get in contact with valleys of each screw thread. Therefore, when the contact screws 551 and 554 are rotated by operation of the contact screw driving motor 552, the tubes 540 getting in contact with the valleys of each screw thread are rotated.

Figure 14:
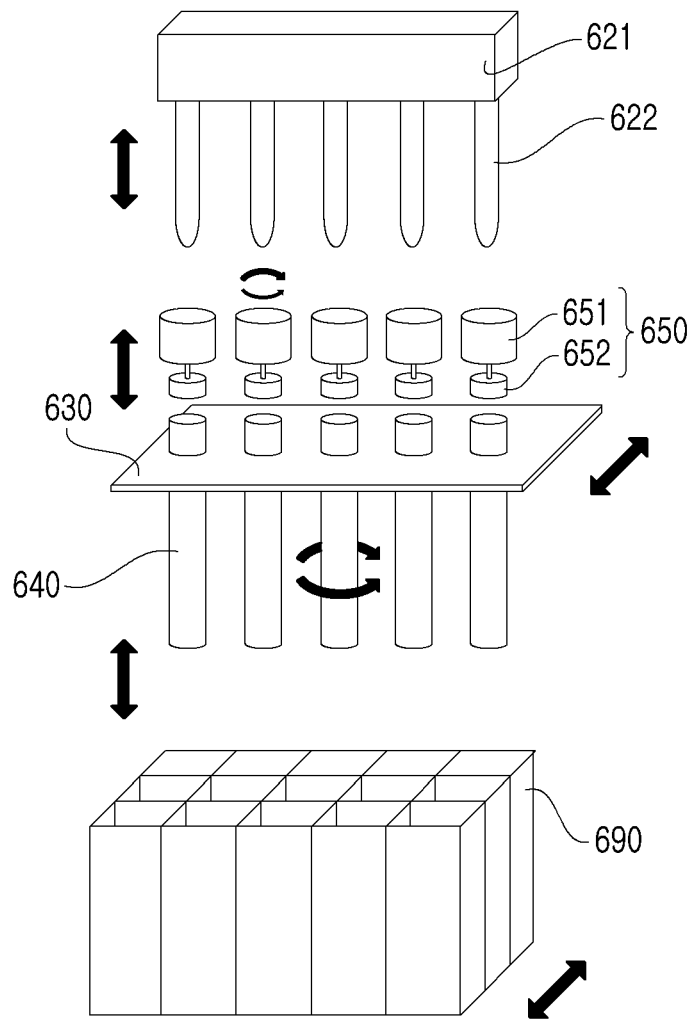

FIG. 14 is a conceptual diagram showing a biological material extraction apparatus according to a seventh preferred embodiment of the present invention. The extraction apparatus illustrated in FIG. 14 includes a magnet support part 621, magnets 622, a tube support part 630, and a tube rotating part 650. The extraction apparatus illustrated in FIG. 14 may further include components for horizontally moving and lifting the magnet support part 621, the tube support part 630 and a cassette 690. However, the seventh embodiment is different from the above embodiments in the structure of the tube rotating part 650 for rotating the tubes 640.

The tube rotating part 650 includes a tube rotating motor 651 and a tube cover 652. The tube rotating motor 651 and the tube cover 652 are applied to each tube 640. When the tube rotating motor 651 linked with the tube cover 652 is operated after the tube cover 652 is tightly fit to the open upper portion of the tube 640, the tubes 640 are individually rotated to stir the solution.

As described above, the biological material extraction apparatus according to the present invention can effectively extract biological materials by intensely mixing the solution through rotation of the tubes. Furthermore, various embodiments to rotate the tubes are illustrated in the drawings, and besides the above, various rotational mechanisms can be applied.

While the present invention has been particularly shown and described with reference to exemplary embodiments thereof, it will be understood by those of ordinary skill in the art that various changes, modifications and equivalents may be made therein without departing from the technical idea and scope of the present invention and such changes and modifications belong to the claims of the present invention.

The invention claimed is:
1. A biological material extraction apparatus comprising:
a cassette seating part on which a cassette having a plurality of cells is seated;
a cassette transferring part configured for transferring the cassette seating part;
a tube support part located above the cassette seating part configured to support tubes that are arranged to be inserted into the cells of the cassette;
a tube lifting part configured for vertically lifting the tube support part;
a magnet support part located above the tube support part configured to support magnets that are arranged to be inserted into the tubes supported by the tube support part;
a magnet lifting part configured for vertically lifting the magnet support part;
a tube rotating part configured for rotating the tubes when the tube support part is lowered and the tubes are inserted into the cells of the cassette; and
a rotary support part configured for getting in contact with and supporting the tubes at the opposite side of a first contact part of the tube rotating part when the first contact part gets in contact with sides of the tubes,
wherein the tube rotating part comprises:
a first motor, including a first rotary shaft, for generating rotary power;
a pinion gear engaged with the first rotary shaft of the first motor; and
the first contact part configured for getting in contact with the sides of the tubes and having a rack gear saw-tooth coupled with the pinion gear at a predetermined point,
wherein the rotary support part comprises:
a second motor, including a second rotary shaft, for generating rotary power:
a support block connected with the second rotary shaft of the second motor, and
a second contact part connected with the support block such that the second contact part is off-centered from a rotational center of the support block, the second contact part extending in parallel with the second rotary shaft of the support block,
wherein the first contact part of the tube rotating part is movable in a horizontal direction while the second contact part of the rotary support part is unmovable in the horizontal direction,
wherein coating material is provided on the surface of the first contact part getting in contact with the tubes so that the tubes are rotatable by a frictional force of the coating material provided on the first contact part,
wherein a concave tube support groove is formed at a point where the second contact part gets in contact with the tubes, the tubes being stably supported and rotated seated on the tube support groove.

* * * * *